(12) United States Patent
Sigrist

(10) Patent No.: US 6,872,810 B1
(45) Date of Patent: Mar. 29, 2005

(54) BIOCHEMICAL SENSOR SYSTEM WITH INCREASED SENSITIVITY BY MOLECULAR AMPLIFICATION OF SIGNAL

(75) Inventor: Hans Sigrist, Kernenried (CH)

(73) Assignee: Centre Suisse d'Electronique et de Microtechnique SA, Neuchatel (CH)

( * ) Notice: Subject to any disclaimer, the term of this patent is extended or adjusted under 35 U.S.C. 154(b) by 0 days.

(21) Appl. No.: 10/031,068

(22) PCT Filed: Jul. 10, 2000

(86) PCT No.: PCT/EP00/06513

§ 371 (c)(1),
(2), (4) Date: May 29, 2002

(87) PCT Pub. No.: WO01/06002

PCT Pub. Date: Jan. 25, 2001

(30) Foreign Application Priority Data

Jul. 16, 1999 (FR) ............................... 99 09258

(51) Int. Cl.$^7$ .......................... C07H 19/00; C12Q 1/68
(52) U.S. Cl. .......................................... 536/22.1; 435/6
(58) Field of Search ............................. 536/22.1, 23.1; 435/6, 287.2; 436/524, 530, 535

(56) References Cited

U.S. PATENT DOCUMENTS 5,690,894 A * 11/1997 Pinkel et al. .............. 422/68.1
5,795,738 A * 8/1998 Grandi et al. .............. 435/69.1
5,858,802 A * 1/1999 Chai-Gao et al. ........... 436/524
6,238,866 B1 * 5/2001 Yeh et al. ...................... 435/6
6,261,779 B1 * 7/2001 Barbera-Guillem et al. ... 435/6
6,406,894 B1 * 6/2002 Hoersch et al. ............... 435/97

FOREIGN PATENT DOCUMENTS

WO  WO 97/27317  * 7/1997

* cited by examiner

Primary Examiner—Jeffrey Fredman
Assistant Examiner—Suryaprabha Chunduru
(74) Attorney, Agent, or Firm—Sughrue Mion, PLLC

(57) ABSTRACT

The present invention provides a simplified method for identifying differences in nucleic acid abundances (e.g., expression levels) between two or more samples. The methods involve providing an array containing a large number (e.g. greater then 1,000) of arbitrarily selected different oligonucleotide probes where the sequence and location of each different probe is known. Nucleic acid samples (e.g. mRNA) from two or more samples are hybridized to the probe arrays and the pattern of hybridization is detected. Differences in the hybridization patterns between the samples indicates differences in expression of various genes between those samples. This invention also provides a method o end-labeling a nucleic acid. In one embodiment, the method involves providing a nucleic acid, providing a labelled oligonucleotide and then enzymatically ligating the oligonucleotide to the nucleic acid. Thus, for example, where the nucleic acid is an RNA, a labeled oligoribonucleotide can be ligated using an RNA ligase. In another embodiment, the end labelling can be accomplished by providing a nucleic acid, providing labelled nucleoside triphosphates, and attaching the nucleoside triphosphates to the nucleic acid using a terminal transferase.

17 Claims, 2 Drawing Sheets

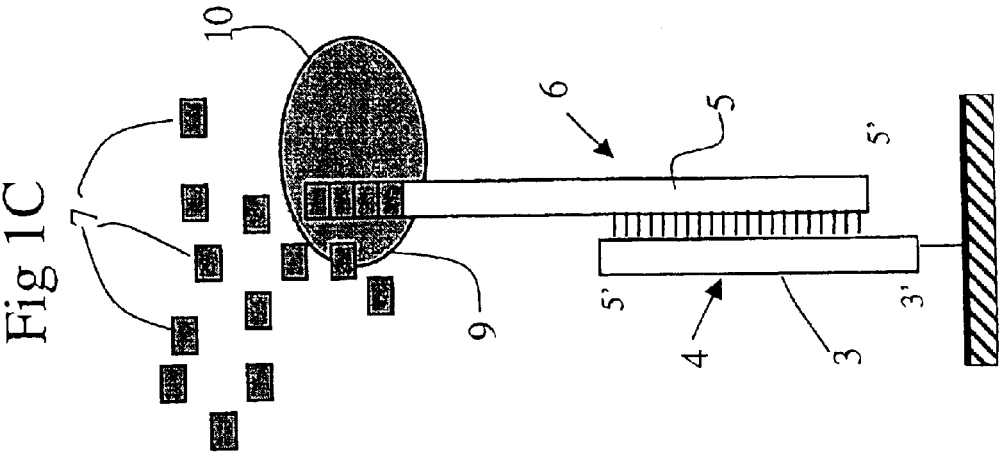
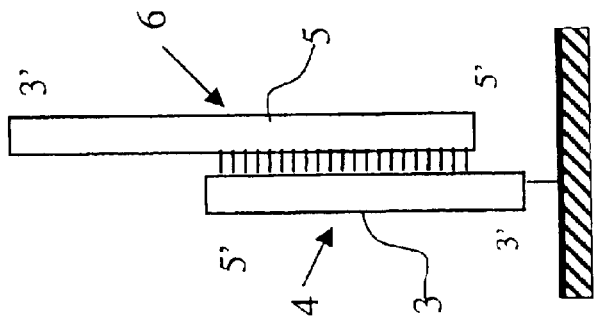
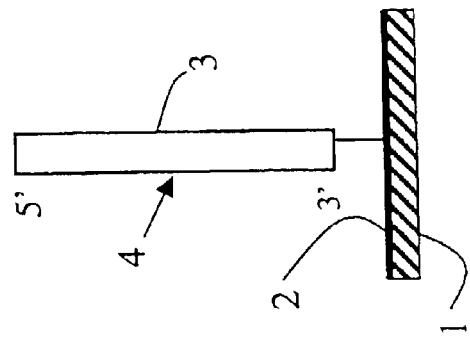

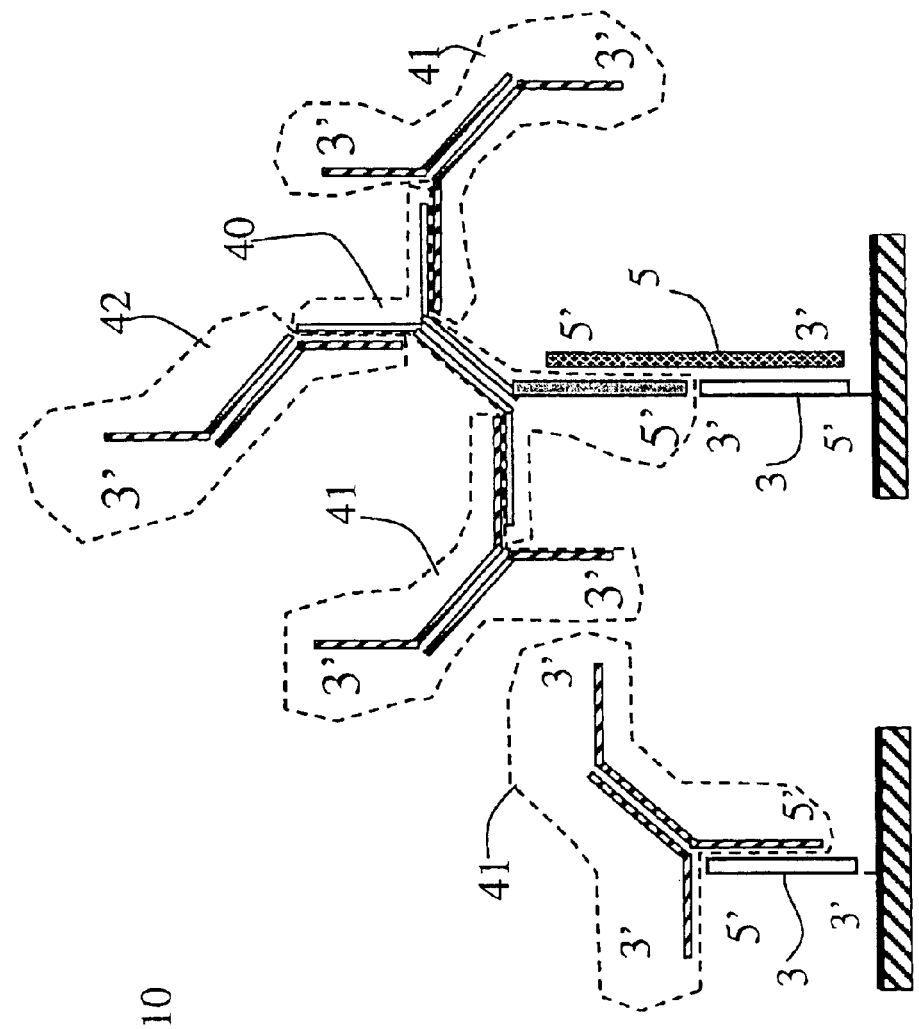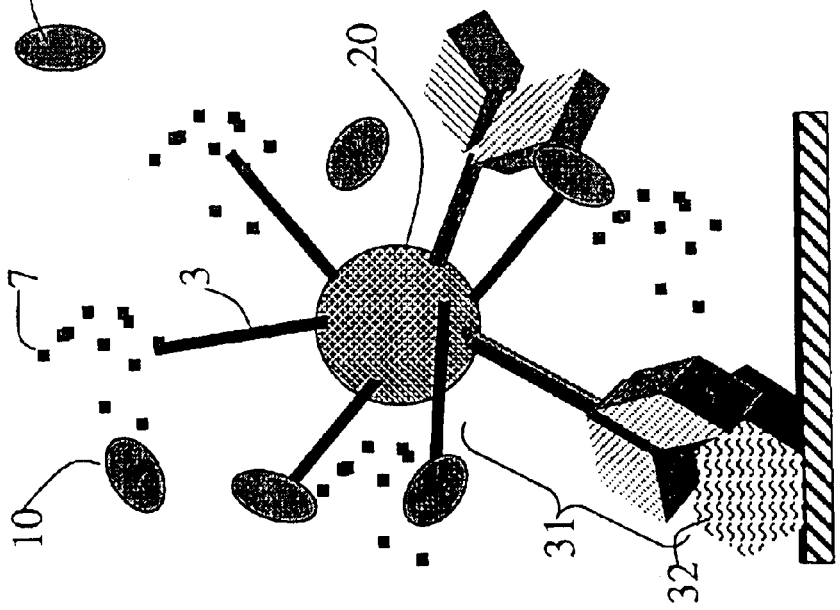

BIOCHEMICAL SENSOR SYSTEM WITH INCREASED SENSITIVITY BY MOLECULAR AMPLIFICATION OF SIGNAL

BACKGROUND OF THE INVENTION

The present invention concerns a biochemical sensor system whose sensitivity is increased by molecular amplification of a signal initialised by the interaction between a biochemical entity present in a solution or a biological fluid and a reagent immobilised on the substrate of the sensor and having a specific affinity for said biochemical entity.

In the field of biological sensors, systems are increasingly sought which allow the limits of detection and analysis of biological entities in biotic fluids to be pushed back further, in the hope of obtaining very high detection sensitivity. Thus, technological improvements have concerned not only the instrumental environment, for example the limits for detecting a signal, but also the design of the sensor itself as soon as limits of sophistication were attained at the instrumental level. But even here, improvements at the sensor level have reached a threshold beyond which it is no longer possible to detect the biomolecules in the form of traces such threshold being of the order of a nanomolar (nM) or picolmolar (pM).

Nonetheless, other improvements have enabled the sensor signal, until then undetectable by former technologies, to be measured owing to an amplification of the signal on which the detection principle relies. Such amplification finds its preferred application in the field of biological sensors given that the conditions implemented in biological analysis are compatible with bio-amplification systems.

Currently, two bio-amplification modes are employed in systems intended to detect, for example, immunological reactions. According to a first amplification mode, in ELISA (Enzyme Linked Immunosorbent Assays) tests, the molecule to be detected, for example an antibody which interacts with a chemical entity such as an immobilised antigen, is chemically linked to an enzyme. The enzyme is used to catalyse the transformation of the detectable molecules. In the currently used ELISA systems, the enzymes which catalyse the production of chemical entities are almost always hydrolases. The water soluble reaction products are preferably detected in the whole reactional medium by measuring absorption, luminescence or bioluminescence.

In biosensors, a second amplification mode is obtained by increasing the number or mass of species detected. This amplification principle is achieved for example by linking mass markers to the molecule to be detected.

If the detection principle relies on fluorescence or absorption, fluorescent or absorbent molecules are chemically linked to the chemical entity. By way of an example of this type of amplification, U.S. Pat. No. 5,175,270 may be cited, which discloses an amplification mechanism from a dendrimer architecture at the surface of the sensor. The modified molecule link on each molecule targeted, or the marked secondary reagent link (for example colloids, nanoparticles or fluorophore-labelled secondary antibodies will produce linear signal amplification. Latex balls, semiconductor nanocrystalline compounds or colloidal gold are mass markers currently used in biosensor systems. In commercial amplification systems, secondary antibodies strongly marked by fluorescent molecules contribute to increasing the signal in a linear manner.

Generally, the usual systems amplify the sensor signals via reactions catalysed by an enzyme which increases the number of secondary chemical entities in the medium by catalysis (catalytic amplification for global detection). Otherwise, the sensor signals are increased either by adding mass, for mass sensitive detection, or by increasing the number of labelled molecules which are linked to the unit.

By way of example of linear amplification at the surface of a sensor, fluorescent signal amplification may be cited: in this system the secondary antibodies are conjugated to allow detection of targets in small quantities.

These two amplification modes which have just been briefly described have allowed detection sensitivity to be substantially increased, either in solution or on a surface: they do not however allow a sufficiently high signal to be obtained to make them able to be used sufficiently in practice.

SUMMARY OF THE INVENTION

The object of the present invention is thus to further increase the sensitivity threshold of a biochemical sensor via an amplification method lacking the drawbacks of the prior art, while being particularly simple to implement and less expensive.

The present invention thus concerns a biochemical sensor with molecular signal amplification for detecting and analysing a biological entity in a biotic medium, this biological entity being able to include oligonucleotides, peptides or polysaccharides. The amplification system is characterised in that monomer compounds and catalytic units are added to the biotic medium, said catalytic units being capable of catalysing, from the end of an elementary strand of the biological entity, a polymeric concatenation of said monomer compounds thus locally increasing a physical parameter which can be measured at the sensor surface.

The catalytic units are enzymes selected from among all the classes of transferases, polymerases and synthases which it is possible to use, either individually, i.e. only selecting a single enzyme class, or by selecting several enzymes which are used in combination or added sequentially to the biotic medium.

Among the preferred catalytic units, a specific transferase of DNA or simple RNA which extends the oligonucleotide strand can be cited.

The monomer compounds, which are added to the biotic medium to locally increase mass by polymerisation, are preferably selected from among nucleic acids: NTP or dNTP; wherein N=A (Adenosine), C (Cytidine), G (Guanosine) or T (Tymidine) and d=deoxy.

The peptidases, used in conditions which favour the inverse reaction, enable proteinaceous materials to synthesise. When one wishes to obtain a local carbohydrate mass increase by a sequential addition of enzymes, transferases monosaccharides are preferably chosen.

As indicated hereinbefore, detecting and analysing a chemical entity in a biotic medium according to the invention fundamentally relies on an increase in a measurable parameter, such as mass, at the actual surface of the sensor.

According to a first detection mode, the sensor surface has a waveguide or waveguide gradient arrangement allowing detection, for example by optical means in the evanescence field of a variation in the refractive index resulting from the variation in mass at the sensor surface, this variation correlating with the analysis of the biochemical entity.

According to a second detection mode, the monomer compounds added to the biotic medium are marked with a chromophor or fluorophor, so that the polymer formed will increase locally the marking density and allow a fluorescence measurement to be taken which correlates with the analysis of the biochemical entity.

These two detection modes are given by way of example, but the sensor system according to the invention can be adapted to any other type of biosensor sensitive to an increase in a physical parameter, such as surface mass.

It is thus necessary to keep the elementary strand of the elementary entity at the sensor surface, allowing for example mass increase by polymerisation from one of its ends. The substrate thus undergoes a suitable treatment, explained in more detail hereinafter, which allows the detection unit to be immobilised directly or indirectly.

Direction immobilisation of the detection unit is achieved by a covalent or non covalent interaction with the chemical entity to be detected, said interaction being able to be one directional for example being established by one of the ends of the nucleotide sequence.

Such immobilisation may also be achieved by using a photopolymerisable cross linkaging agent.

When immobilisation is achieved indirectly, a molecular structure is used which allows a larger number of detection units to be immobilised, said molecular structure itself being linked to the surface of the biosensor by a docking unit. Optimally, this docking unit has a great affinity for interacting with the detection molecules. Such interactions are for example interactions of the (first antibody)-(second antibody) type, as is the case in generalised ELISA test protocols, or interactions of the DNA/DNA type as is the case in DNA based biosensor devices.

Numerous structures can be used to form the molecular structure, amongst which the following can be cited:

small molecular entities which allow at least a dual functionalisation such as a hetero-bifunctional cross linkage agent for example N-(m-(trifluromethyl) diazirin-3yl)phenyl)-4-maleimido-butyramide, an antibody modified with an oligonucleotide or one of its fragments. The hydrocarbonated fraction and the key-part of the antibodies have functional groups such as carbohydrate lateral chains and amino-acids which respectively facilitate the addition of oligonucleotides, DNA dendrimers of suitable sizes, which are of great interest because of their aptitude for multiple functionalisations for specific oligonucleotides. Extensions to a single strand of DNA dendrimers allows functionalised antibodies to be fixed using oligonucleotides, metal or semiconductor nanocrystalline compound colloids which provide the essential elements for multiple functionalisation.

The docking unit which establishes a selective link between the molecular structure and the detection molecule, in a preferred embodiment, is formed by a part of an identical molecule to the detection unit, such as an antibody or a fragment thereof. Amongst the docking units able to be used within the scope of the present invention, the following may be cited:

all the immunoglobuline classes, protein A, protein G, fusion protein A-G, avidine, neutravidine, streptavidine and oligonucleotides which occupy a quarter of the individual biotin link sites, a labelled polyhistidine, a labelled nitrolo-tetraacetate, any type of specific but not covalent link molecular interaction.

As a function of the features of the scaffold, and in particular when it has a dendrimer architecture, the polymer linking unit can be an oligonucleotide with a sequence of nucleotides partly complementary to one of the branches of a dendrimer.

BRIEF DESCRIPTION OF THE DRAWINGS

Other features and advantages of the invention will appear in the following description made with reference to the annexed drawings, in which:

FIGS. 1A, 1B and 1C show schematically the steps leading to a first embodiment,

FIG. 2 is a schematic diagram of a second embodiment, and

FIGS. 3A and 3B show schematically a third embodiment.

DETAILED DESCRIPTION OF THE INVENTION

A first embodiment of the simplest sensor system according to the invention will now be described, with reference to FIGS. 1A, 1B and 1C which show schematically the steps allowing a signal to be amplified.

The first step (FIG. 1A) shows a sensor 1 at the surface 2 of which an oligonucleotide 3 is immobilised by its end 3'. This oligonucleotide 3 is more generally designated "detection molecule 4". This immunobilisation may be effected either by a suitable treatment of the sensor surface to allow a covalent link to be established with end 3' of oligonucleotide 3, or by a thermochemical method or by a photo-immobilisation technique by means of a polymerisable cross linking agent, as will be explained in more detail in the following examples. This detection molecule includes a specific nucleotide sequence which, via hybridisation (FIG. 1B) will allow an elementary strand 5 of the biochemical entity 6 to be analysed to be immobilised, this elementary strand having a complementary nucleotide sequence to that of detection molecule 4. This hybridisation is effected by leaving end 3' of elementary strand 5 free. In the next step (FIG. 1C), monomer nucleotides 7 have been added, hereinafter designated by the usual abbreviation dNTP, and an enzyme 10, such as a transferase at end 3'. This enzyme 10 will specifically catalyse the formation of covalent links between end 3' of elementary strand 5 and successively the nucleotides added to the medium to create a polymer chain formation 9 which will increase the total mass at the surface, which will mean a measurable variation in the refractive index. In the event that the nucleotides added to the medium are labelled with a fluorescent label, this increase in mass will mean an accumulation of labelled nucleotides at the surface of the sensor and a global decrease in fluorescence in the medium.

FIG. 2 shows a sensor system according to the invention with a more complex amplification mode, in that oligonucleotides 3 are indirectly linked to surface 2 of sensor 1 via a scaffold 20 immobilised at the sensor surface by a docking unit 30. In the example shown, scaffold 20 is formed by a bifunctionalised colloid in order to keep both oligonucleotides 3 attached by end 5' and an antibody fragment 31 complementary to an antigen 32 immobilised at the surface, antibody 31 and antigen 32 together forming the docking unit. In order to amplify the signal, one proceeds as previously indicated by adding an enzyme 10 and nucleotides 7.

The description above gives, in detail, the different steps which allow a biochemical sensor system according to the invention to be obtained and the modifications which need to be made to the surface of an optical sensor of the type which relies on fluorescence detection or refractometric detection. With minor modifications, the procedures described also apply to other sensor systems and to other transducer materials. Surface modification by silanisation is suitable for surfaces which give surface hydroxy groups or for surfaces on which hydroxy groups can be produced. In a different way, photo-immobilisation technologies are also used to functionalise a surface when one wishes to have an addressable functionalisation surface and remove non specific links of the biological entity from the medium. In theory, the materials used for the sensor are metallic oxides both for measurements based on refractometry and for those based on fluorescence. Modifications by amplifying scaffold have been performed with gold colloids and dendrimers with several branches. In all the examples described hereinafter, the signal amplification was performed with the transferase at end 3' (3'TT) for catalysing the addition of nucleotides at free end 3'.

I. Functionalisation of the Sensor Surface and Immobilisation of the Detection Unit Surface Silanisation of a Metallic Oxide and Oligonucleotide Link Starting from the protocols of R. E. Kunz described in the publications "Sensor and Actuators A (1997) 60,23" and "Sensors and Actuators B (1997) 38–39, 705", the number of hydroxy radicals was increased by treating the optical sensors duplicated on organic polymers with an oxygen plasma in a plasma generator. The optical sensor systems were cleaned on glass via ultrasound in 65% nitric acid for thirty minutes (30 nm), then rinsed in bidistilled water. The external metallic oxide surfaces were silanised in vapour phase with 3-(glycidyloxy) propoly-trimethoxysilane for two days at 180° C. and 10 mbar. Finally, commercial oligonucleotides with an end chain 3' or 5'amino previously dissolved in a sodium phosphate buffer diluted to 1/100 were immobilised on the epoxy surfaces thereby obtained.

Immobilisation of Oligonucleotides via Photopolymerisable Polymers

According to a protein photo-immobilisation protocol described by H. Gao et al (Biotechnol. Appl. Biochem. (1994) 20, 251–263), the addressable immobilisation technique of biomolecules has been extended to the covalent link of oligonucleotides. Both, layer coating and immobilisation in a single step, were revealed as being applicable to nucleotides. Instead of using modified aryldiazirine bovine serum albumin, a modified aryldiazirine dextran was used by way of a new reagent as photopolymerisable polymer. A modified aryldiazirine dextran (T-dextran) was synthesised by thiocarbamolyation of the amino-dextran with the 3-(trifluoromethyl)-3-3(m-isothiocyanophenyl) diazirine. For photo-immobilising the oligonucleotides, a solution was prepared containing 20 nanomoles of T-dextran and 10 nanomoles of oligonucleotides in solution in a buffer medium at pH 7.4 (1.5 nM of NaCl and 0.05 mM of sodium phosphate).

This mixture was used to jet printing a surface of 10 mm$^2$, which corresponds to a density of 500 fmol/mm$^2$, i.e. 5 nl for a surface of 3×3 mm. Once this deposition has been performed, the samples are dried at ambient temperature for 2 hours at 20 mbar, then they are exposed to light to activate the cross linking of the polymer. This immobilisation was effected by irradiation for three minutes with an Orvel light source (11 mW/cM$^2$) with a filter to remove radiation less than 320 nm. The modified surfaces are washed by several buffer solutions and finally five times in bidistilled water. By isotopic labelling, it was determined that 40% of the oligonucleotides were immobilised on the sensor, which approximately corresponds to a density of 200 fmol/mm$^2$.

Oriented Oliogonucleotide Immobilisation

In order to have oriented oligonucleotide immobilisation, substrates were prepared with silicon nitride, organic polymers, diamond or DLC (Diamond-like Carbon) at their surface. The base substrates, with the exception of the organic polymers, are ultrasound washed successively 5 mm each time in hexane and in ethanol and dried for two hours at ambient temperature at 6 mbar. A drop of a 0.25 mM ethanolic solution of the cross linking agent N-(m-(trifluromethyl)diazirin-3yl)phenyl)-4-malemidobutyramide is then deposited with a syringe. A drop of 10 μl covers a surface of 25 mm$^2$. After drying for two hours at ambient temperature at 30 mbar, the photo-immobilisation is effected by irradiating the samples for 20 nm with a Stratalinker light source at 350 nm providing an irradiation of 0.9 mW/cm$^2$. The modified surfaces are then washed three times with hexane and ethanol; in the case of an organic polymer used as a substrate, methanol will be used as washing product. In order to obtain covalent immobilisation, 10 nmol of 5'thio-oligonucleotide are dissolved in 50 μl of a degassed buffer solution at pH 7.7 (0.2 M HEPES+1 mM EDTA). This solution is then deposited by pipette onto the modified maleimide surface and incubated for sixteen hours at ambient temperature. Finally, as explained hereinafter, the modified oligonucleotide surface is rinsed with the hybridisation buffer solution.

II Preparation of the Scaffold

Gold Colloid Functionalisation with Oligonucleotides and Antibody Fragments F(ab')

Gold colloids with a diameter of 20 nm are sedimented (10,000 revolutions/mn for 30 nm) then the elements floating on the surface are removed and a solution containing 0.7 nmol of 5'thio-oligonucleotides and freshly prepared 0.3 nmol of fragments F(ab') dissolved in 50 μl of a degassed buffer solution at pH 7.7 (0.2 M HEPES+1 mM EDTA) is added. The solution is kept at ambient temperature for sixteen hours and the modified colloids are washed by effecting three cycles of sedimentation and suspension in a sodium phosphate buffer.

Scaffold of DNA Tri and Multidentates

With a tridentate DNA structure, there is a DNA with two ends 3'OH and for the first dendrimer generation with five ends 3'OH.

The dendrimer architecture of this scaffold was prepared as indicated in the patents of the Polyprobe company (U.S. Pat. No. 5,175,270; U.S. Pat. No. 5,484,904; U.S. Pat. No. 5,487,973). DNA oligonucleotide sequences were selected taking account of an efficient link of the complementary strand. A basic dendrimer structure 41 was assembled (FIG. 3A) leaving the two ends 3' free for amplification 3TT, an end 5' being complementary to the detection molecule immobilised on the surface. This molecular design allows the number of extension sites 3TT to be duplicated. The first generation dendrimer molecular structures were designed in a similar manner. The addition of a tetradentate dendrimer (40) and a second stage to the tridentate dendrimers (41) and bidendate dendrimers (42) brought the number of extension sites 3TT to five (FIG. 3B).

Hybridation of Complementary DNA Strands and End 3' Transferase Reaction

III Hybridisation of the DNA Oligonucleotides with the Surface Immobilised Detection Molecules The hybridisation reaction was effected with detection molecules immobilised at the surface, i.e. with 15 to 60 nucleotides. After immobilising the DNA detection molecules, the surfaces were washed three times with a solution of 5×SSC containing 0.1% by weight of sodium dodecylsulphate to remove the oligonucleotides absorbed in a non covalent manner. Single chain elementary DNA strands were then dissolved in 250 ml of a hybridisation solution including 1% by weight of casein, 0.1% of lauroyl-sarconsin salt and 0.02% of sodium dodecysulphate in a buffer solution of 5×SSC.

The solution thereby obtained was deposited on the sensor surface and left to incubate for two hours at 45° C. After the hybridisation step, the surfaces were washed two times with 2×SSC containing 1% by weight of sodium dodecysulphate at ambient temperature and three times with a buffer solution 5×SSG, containing 1% by weight of sodium dodecysulphate, heated to 50° C. These intensive washing operations incorporating detergents are necessary to remove the unhybridised elementary strands.

End 3' Transferase Reaction (Reaction 3TT)

In the next step, nucleotides with or without a fluorescent label were added to the hybridised elementary strands, at the same time as the enzyme 3TT. This enzyme catalyses the nucleotide link with the elementary strand. By adding monomers to the elementary strands, the enzyme increases the refractive index for mass or fluorescence detection at the biosensor surface. The sensor surface was first washed twice with 200 µl of the cacodylate buffer at pH 7 (0.5 M cacodylate, 5 nM $CoCl_2$, 1 mM dithiothreitol). The reaction was started by adding two units of 3'TT to an incubation medium composed of 20 µl cacodylate buffer, 100 µl of a deoxynucleotide phosphate (dNTP), 4 µl of 5 nM of dCTP and 100 µl of water. The mixture was briefly mixed by pipette suction and deposited on the substrate.

The refractive index modifications at the sensor surface were followed either optically with an integrated optical sensor, or by fluorescence detection. The signal amplification was quantified by working out the difference between the highest signal obtained from a surface having the immobilised elementary strand, and the signal originating from a reference sensor in which the elementary strand did not undergo any hybridisation.

IV Signal Amplification in a Genetic Test

Fluorescence Signal Amplification Detection Test

In this test, DNA detection molecules were immobilised at the surface of the sensor by dextran-based photo-immobilisation and hybridised with the oligonucleotides which are, either a synthetic reference compound or an oligonucleotide originating from PCR. In the 3'TT reactional medium, there are "dCTP"s and ChromaTide BODIPY FL-14-dCTP fluorescent nucleotides (Molecular Probes, Eugene, Oregan, USA). The amplification reaction was initiated by adding two units of 3'TT and stopped after five minutes by washing the surface of the sensor with the reaction buffer solution. The increase in surface fluorescence was followed and the results compared with the fluorescence after hybridisation of a detection molecule labelled with fluorescein.

In a second series of experiments, the oligonucleotide was hybridised both with the linking branch of the first generation of dendrimers and with the surface-linked detection molecule. With this configuration, the 3'TT reaction occurred with five ends 3' available on the molecular structure.

The incorporation of the fluorescent dCTP compounds was recorded. The experiment results shows that the signal is increased by a factor of 3.8 compared to that of a biosensor arranged without dendrimers.

V. Amplification of the 3'TT Signal in Immunological Tests

The link of an antibody to a photo-immobilised antigen was examined using the integrated optical detection without any labels as described by H. Gao et al (Biosensors and Bioelectronics (1995) 10, 317–328). The test was effected with an unmodified antibody and, in a second series of experiments, with an antibody functionalised with an oligonucleotide. The antibody was functionalised as indicated by Ghosh et al (Bio-conjugate. Chem. (1990) 1,71–76). The secondary signal amplification via the 3'TT reaction was effected for both of the test systems. The reactional medium included "dCTP" and two units of the enzyme 3'TT. The mass increase was followed over time by observing the modifications in the refractive index. The initial reaction speed and the saturation level were 64 times greater with the sample including the oligonucleotide modified antibody than with the sample without any oligonucleotides.

An increase by a factor of 150 was achieved for the detection sensitivity of a biological entity with a bi-functionalised gold colloid molecular structure having at its surface both specific antibody fragments of an antigen and oligonucleotides. This molecular arrangement was use to amplify the signal of an immunological biosensor. As described hereinbefore, particles of colloidal gold of 10 nmoles were modified with oligonucleotides and F(ab') fragments in a proportion of 7/3. These bi-functionalised gold colloids were then applied to the surface of the biosensor at the same time as two 3'TT units and the mass increase was recorded over time. The antigenic determining factor of the F(ab') fragment immobilised on the colloid is oriented towards an antibody epitope of the ELISA test. The signal amplification as a function of mass was obtained first of all by means of a selective link of the substituted colloids. The increase in the oligonucleotide chain caused by the 3'TT reaction leads to a great increase in the signal. This eventually leads to saturation amplification 150 times greater than that of a sample without any colloids.

What is claimed is:

1. A biochemical sensor system with molecular amplification of a signal for detecting and anal sing a biological entity in a biotic medium, said biological entity being identifiable by at least an elementary strand including a specific nucleotide sequence, said sensor having at its surface a directly or indirectly immobilised detection unit, said detection unit having a complementary nucleotide sequence to that of the biological entity, and said sensor surface being arranged to supply to a detection and measuring device a signal representative of the increase in mass via hybridisation of the biological entity with the detection unit, characterised in that the biotic medium contains monomer compounds and enzymatic catalytic units selected from a DNA strand 3' terminal transferase, a RNA strand polymerase and a synthetase, said enzymatic catalytic units catalyzing from the end of an elementary strand of the biological entity, a polymeric concatenation of said monomer compounds thus locally increasing the mass by a chain extension inducing an amplification of the signal which can be measured at said sensor surface, said sensor system being further characterised in that the compounds allowing the scaffold to be formed are selected from among an antibody modified by a nucleotide, or one of its fragments, DNA dendrimers of suitable size, and metal or semiconductor nanocrystalline compound colloids.

2. Sensor system according to claim 1, characterised in that said signal which can be measured is absorption of a light wave or emission of a fluorescence signal.

3. Sensor system according to claim 1, characterised in that the enzymes are added to the biotic medium by selecting a single kind of enzyme, by combining several kinds or by adding several kinds sequentially.

4. Sensor system according to claim 1, characterised in that the biological entity is a peptide or a protein and in that the enzyme is a peptide synthetase.

5. Sensor system according to claim 4, characterised in that the biological entity is a di- or oligo-saccharide and in that the sequentially added enzymes include a mono- or oligo-saccharide transferase.

6. Sensor system according to claim 1, characterised in that the monomer compounds are selected from among nucleotides and oligonucleotides.

7. Sensor system according to claim 1, characterised in that the sensor surface has a waveguide or waveguide gradient arrangement allowing optical detection of the refractive index variation, linked to the variation in mass at the sensor surface, this refractive index variation being able to be correlated with the analysis of the biochemical entity.

8. Sensor system according to claim 1, characterised in that the monomer compounds are labelled with a chromophor or a fluorophor allowing an absorption or fluorescence measurement to be made which can be correlated with the analysis of the biochemical entity.

9. Sensor system according to claim 1, characterised in that the sequence of nucleotides forming the detection unit is directly linked to the surface of the sensor by a covalent link.

10. Sensor system according to claim 1, characterised in that the detection unit is linked in a one-directional manner by its end (3' or 5').

11. Sensor system according to claim 1, characterised in that the nucleotide sequence forming the detection unit is linked to the surface of the sensor by photo-immobilisation.

12. Sensor system according to claim 1, characterised in that the nucleotide sequence forming the detection unit is indirectly linked to the sensor surface by a bi-functional scaffold, which is itself linked to said surface by a docking unit.

13. Sensor system according to claim 12, characterised in that the compounds allowing the docking unit to be formed are selected from among immunogloblins, protein A, protein G and amalgamated protein A-G.

14. Sensor system according to claim 12, characterised in that the compounds allowing the docking unit to be formed are selected from among avidine, neutravidine, streptavidine and DNA or RNA oligonucleotides occupying a quarter of the biotin link sites.

15. A biochemical sensor system with molecular amplification of a signal for detecting and analysing a biological entity in a biotic medium, said biological entity being identifiable by at least an elementary strand including a specific nucleotide sequence, said sensor having at its surface a directly or indirectly immobilised detection unit, said detection unit having a complementary nucleotide sequence to that of the biological entity, and said sensor surface being arranged to supply to a detection and measuring device a signal representative of the increase in mass via hybridisation of the biological entity with the detection unit, characterised in that the biotic medium contains monomer compounds and enzymatic catalytic units selected from a DNA strand 3' terminal transferase, a RNA strand polymerase and a synthetase, said enzymatic catalytic units catalyzing from the end of an elementary strand of the biological entity, a polymeric concatenation of said monomer compounds thus locally increasing the mass by a chain extension inducing an amplification of the signal which can be measured at said sensor surface, said sensor system being further characterized in that the nucleotide sequence forming the detection unit is indirectly linked to the sensor surface by a bi-functional scaffold, which is itself linked to said surface by a docking unit, and in that the compounds allowing the docking unit to be formed are selected from among a polyhistidine and a nitroloacetate.

16. Sensor system according to claim 14, characterised in that the docking unit is formed by an oligonucleotide having a partially complementary nucleotide sequence to one of the branches of a dendrimer when the molecular structure has a dendrimer architecture.

17. Sensor system according to claim 1, characterised in that the compounds allowing the scaffold to be formed also include a hetero-bi-functional cross linking agent.

\* \* \* \* \*